(12) United States Patent
Jackson

(10) Patent No.: US 6,440,132 B1
(45) Date of Patent: *Aug. 27, 2002

(54) OPEN HEAD BONE SCREW CLOSURE WITH THREADED BOSS

(76) Inventor: Roger P. Jackson, 6600 Indian La., Mission Hills, KS (US) 66208

( * ) Notice: Subject to any disclaimer, the term of this patent is extended or adjusted under 35 U.S.C. 154(b) by 0 days.

This patent is subject to a terminal disclaimer.

(21) Appl. No.: 09/577,908

(22) Filed: May 24, 2000

(51) Int. Cl.$^7$ .............................................. A61B 17/56
(52) U.S. Cl. .............................. 606/61; 606/72; 606/73
(58) Field of Search .............................. 606/60–66, 73; 601/60; 411/81, 214, 374, 378, 383, 396, 397, 381; 215/201

(56) References Cited

U.S. PATENT DOCUMENTS

| | | |
|---|---|---|
| 5,005,562 A | 4/1991 | Cotrel |
| 5,067,955 A | 11/1991 | Cotrel |
| 5,129,388 A | 7/1992 | Vignaud et al. |
| 5,154,719 A | 10/1992 | Cotrel |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,346,493 A | 9/1994 | Stahurski et al. |
| 5,385,583 A | 1/1995 | Cotrel |
| 5,443,467 A | 8/1995 | Biedermann et al. |
| 5,487,742 A | 1/1996 | Cotrel |
| 5,545,165 A | 8/1996 | Biedermann et al. |
| 5,562,663 A | 10/1996 | Wisnewski et al. |
| 5,643,260 A | 7/1997 | Doherty |
| 5,697,929 A | 12/1997 | Mellinger |
| 6,251,112 B1 * | 6/2001 | Jackson ..................... 606/61 |

FOREIGN PATENT DOCUMENTS

| | | | |
|---|---|---|---|
| WO | WO 94/10927 | 5/1994 | |
| WO | WO 94/26193 | * 11/1994 | ................... 606/61 |

OTHER PUBLICATIONS

*Spine*, Lipcott, Williams & Wilkins, Inc., vol. 24, No. 15, p. 1495.

* cited by examiner

Primary Examiner—David O. Reip
Assistant Examiner—Daniel Jacob Davis
(74) Attorney, Agent, or Firm—John C. McMahon

(57) ABSTRACT

A closure for an open ended medical implant with a pair of spaced arms to maintain a rod or the like in the implant. The closure including a top plate with depending side flanges forming a discontinuous ring that is received about the implant in comparatively low profile from side to side. The closure includes a threaded central cylindrical shaped boss depending from the plate to maintain spacing of the implant arms and secure the closure to the implant. The plate and boss have coaxial bores that receive a set screw. The flanges abut against an outer surface of the arms during use to prevent spreading of the arms.

13 Claims, 5 Drawing Sheets

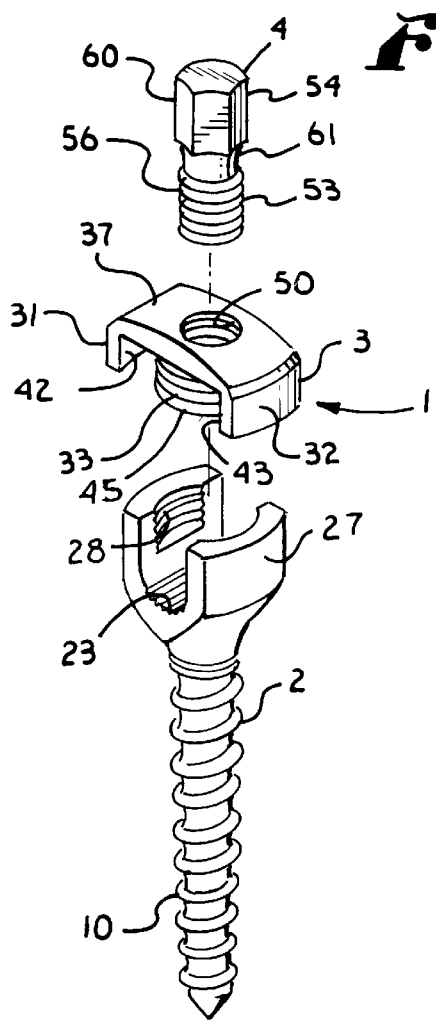
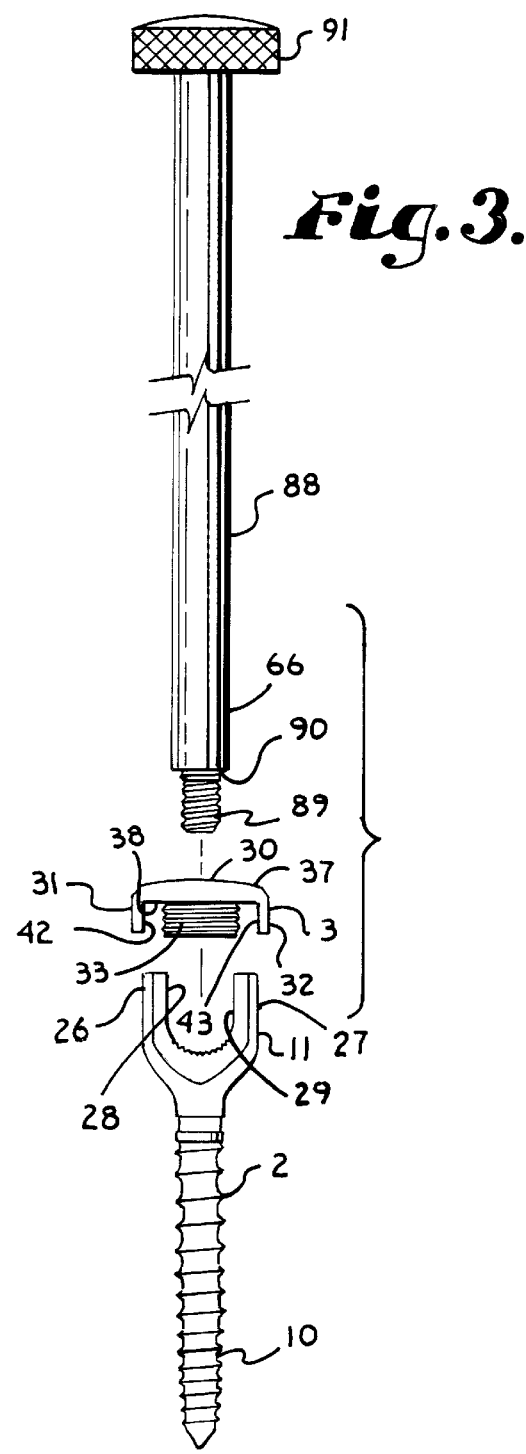

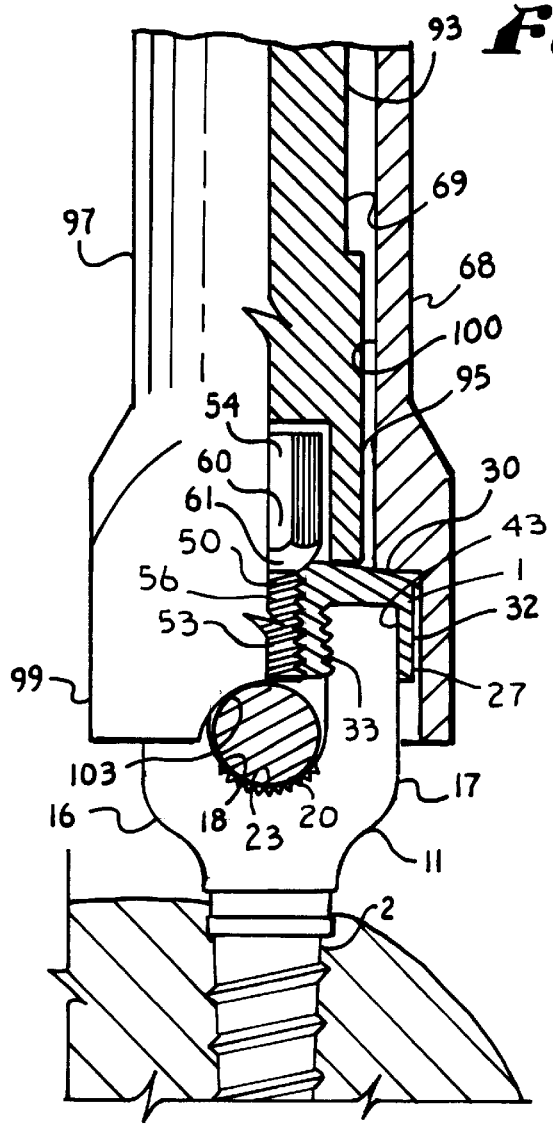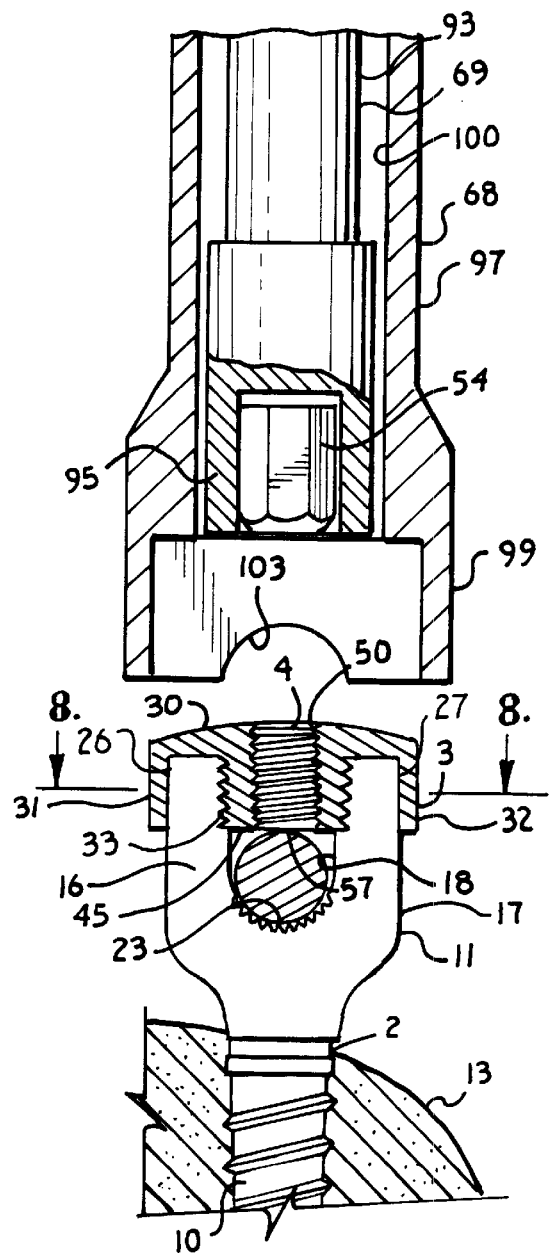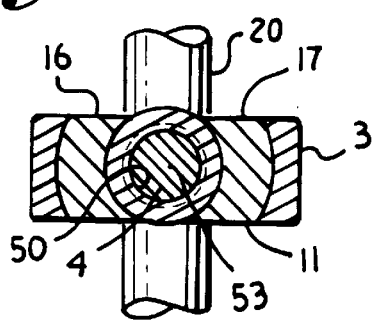

OPEN HEAD BONE SCREW CLOSURE
WITH THREADED BOSS

BACKGROUND OF THE INVENTION

The present invention is directed to a closure for an open-ended medical implant that receives a rod or related rod-like structure in an open end of the implant and then the rod is captured within the end of the implant by the closure.

A wide range of medical implants are utilized within the human body. With respect to the spine these implants include bone screws that are implanted in vertebrae and various types of connectors and the like that are used to interconnect with bone screws and each other to form an overall support matrix or spinal implant system. Many of these implants, especially bone screws, but also hooks and connectors, are open-ended having a yoke with a pair of upstanding arms that receive rods or other structures in a channel formed between the arms. Typically, each yoke receives an elongate rod, but other elements of the system having cylindrical shaped nipples or the like may also be received in the yokes. Because such bone screws and the like are open-ended, some closure must be used in order to capture the rod or other structure received within the open end of the implant.

To insure that the closure remains secured to and on the bone screw or other implant and that the rod or other structure being held in the implant does not slip either axially or rotationally, in many systems a substantial amount of torque must be applied in installing the closure to both maintain the closure in position and urge the closure against the rod so as to lock the rod in position relative to the bone screw or other implant. The force required to torque the closure presents either a destabilizing force to the overall completed implant in that it may spread the arms or alternatively, if the closure has been made in such a way to counteract the destabilizing force of the torque, the closure and overall implant normally are too large to be used effectively within the system or the closure becomes very complex and difficult to manufacture and/or use.

In particular, the prior art has developed plug closures which are simply threaded cylinders that are screwed into threads on the inside of the arms in the open end of the implant to hold the rod or the like in place. High torque exerted on the plug tends to spread the arms during installation or the arms of the implant may later spread due to forces acting on the implant system, thereby loosening the closure and possibly allowing the rod to slip or the plug to work loose from the bone screw.

In addition, the rods are normally curved or non-linear at the location where they are placed in the implant. That is, typically, the spine is not straight and rods used for supporting the spine are bent to follow the curvature of the spine. Consequently, the rod often has a substantial amount of curvature where the closure plugs engage the rod. Because of this curvature, the rod often is somewhat arcuate underneath the plug even after the plug is fully installed. This presents substantial problems, if the rod is later subjected to forces in use in the body, such as where the patient encounters a fall or automobile accident, that cause the rod to bow somewhat against the desired curvature. This then spaces the rod from engagement with the plug or at least reduces the frictional engagement of the plug with the rod to a level that allows the rod to easily rotate or move axially and/or the plug to become loose and even work free of the bone screw over time.

Other types of prior art closure caps are not threadably received as a plug by the implant, but rather have a complex system of interlocking parts with the implant in order to bridge the gap between the arms. Such caps normally slide into place and then are locked by tightening a set screw or the like. Such closures are very difficult to manufacture and are comparatively very expensive. Closures of the slide-in type, in general, are often also difficult to install, because the parts are small and the working space provided to the surgeon during surgery is very limited. Further, the curvature of the rod may make it very difficult to slide the cap into place so that it may then interlock with mating elements in the bone screw.

Yet another type of closure of the prior art has been a closure that provides a ring that goes entirely about the outside of the arms of the implant. Such a ring may be threaded and received on mating threads on the outsides of the arms of the implant. The ring concept works well in preventing the arms of the implant from spreading due to forces. However, this type of system is subject to problems. One of the problems is that like the previous noted system, when the ring secures a curved rod, the rod may later flex so as to release pressure and reduce friction between the closure and rod, so that the rod becomes loose within the implant and can slip by rotation or axial movement therein. Such systems using a plug are usually not very effective in locking the rods in place, equally as the plug normally engages part of the ring and not the rod, so that direct friction of the plug on the rod does not occur.

Furthermore, the outside circumferential ring substantially increases the thickness of the implant along the axis of the rod. This presents a substantial problem, since there is often very limited space along the rod for all of the various connectors, bone screws and the like that are necessary for the overall implant system and such large closures take up too much space. Additionally, the large caps that are necessary for closing this type of implant leave very little room for the surgeons to work and block access of bender devices to the rod that are needed to shape the rod in some types of implant surgery which require that the curvature of the rod to be modified after connection to the bone screws. The large head of such caps is also contrary to the general desire to reduce size, weight and overall volume of such implants so as to reduce their physical impact on the patient.

It is noted that other problems with the prior art include that, while some types of caps prevent outward movement of the arms, such allow the tops of the arms to bend radially inward toward each other so the cap becomes loose. Further, where the cap is threaded and goes over the outside of the arms, it is often very difficult to line up the threads properly between opposite arms and the cap because of the tight working space, so the cap does not sit correctly and does not tighten correctly against the rod.

SUMMARY OF THE INVENTION

A closure cap for an open-ended implant wherein the implant has a pair of upstanding arms located on either side of a rod receiving channel and wherein the arms are interiorly or inwardly threaded to threadably receive the closure. The closure is an incomplete round cap having opposed and equally sized segments or sectors missing so that the cap does not form a complete circle. When positioned to act as a closure, the missing segments allow the closure cap to be comparatively thin in profile relative to a cap of the same radius that is complete. The cap includes an upper plate joined to opposed flanges. The flanges are snugly received around the arms of the implant in use.

The closure includes a central cylindrical member or boss that depends from the plate and is positioned between but in spaced relation to the flanges. The cylindrical boss is sized and shaped to maintain the spacing of the arms when installed on the implant by keeping the arms from bending inwardly. The boss is outwardly threaded to mate with the threads on the interior of the implant arms, so that the boss may be screwed in place between the arms and so that when the boss is fully screwed into the implant head, the flanges are positioned radially outward and in close relationship to the arms to prevent the arms from spreading outwardly.

The plate and the cylindrical boss also include a central top to bottom threaded bore which receives a set screw. In use the set screw engages and is urged under torque against a rod within the channel so as to fix in position and lock the rod against movement relative to the implant.

A set of tools is also provided for use with the invention. A cap installation tool is temporarily threadedly received in the threaded bore to allow the grasping and turning of the closure cap during installation. The installation tool is removed, when the cap is positioned such that the threads of the boss substantially engage and are threaded into the threads of the arms. Once the installation tool is removed and the surgeon is satisfied with the position of the rod relative to the implant, an anti-torque tool is placed over the cap to hold the cap in position and a set screw is positioned within the cap bore. A set screw installation tool is then utilized to torque the set screw which may be a break-off head type wherein the head breaks away at a preselected torque or a non-break-off head type set screw. Once the set screw has been properly torqued, the anti-torque tool and set screw installation tool are removed and the implant is thereafter complete.

A removal tool is also provided which comprises a T-shaped handle with a lower receptacle that receives the cap and allows the cap to be rotated. The cap in this manner can be rotated counterclockwise and removed, should it is necessary to do so for some reason after installation.

OBJECTS AND ADVANTAGES OF THE INVENTION

Therefore, the objects of the present invention are: to provide a closure for an open-ended medical implant that is comparatively thin in profile along an axis of a rod or other structure received in the implant, that resists movement of the upper ends of the implant arms either radially inward or outward subsequent to installation of the cap and that provides a set screw that secures the rod within the implant at the time of installation and at subsequent times when the normal curvature of the rod is bowed during use; to provide such a closure which comprises an upper plate joining a pair of depending flanges that are received around and in touching or abutting relation to the arms of the implant; to provide such a closure wherein the flanges are opposed and together extend approximately 180° about the implant; to provide such a closure having a central depending boss that is threaded to mate with threads on the interior sides of the arms; to provide such a closure in combination with the implant and with a set screw that is highly effective in locking the rod or the like in position relative to the implant and preventing subsequent movement of a rod or other structure either rotationally or axially relative to the implant; to provide such a closure utilizing a relatively small diameter set screw to secure the rod that is much less subject to loosening in comparison to the closure should the rod flex; to provide such a closure which is relatively easy to manufacture and inexpensive to produce; to provide such a closure which is relatively easy to install and may be installed with the rod substantially bent within a rod receiving channel of the implant; to provide such a closure which is relatively easy to remove, should removal be necessary; to provide a set of tools for installing such a closure including an installing tool to facilitate threading of the closure onto the implant; to provide such a set of tools including an anti-torque tool and a set screw installing tool to function in combination to install a set screw in the closure; and to provide a removal tool that captures the closure and allows rotation of the closure relative to the implant; and to provide an overall closure, implant system and set of tools that are especially easy to use and well adapted for the intended purpose thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded view of a medical implant, closure cap and set screw that are used cooperatively in accordance with the present invention.

FIG. 3 is an exploded side elevational view of the medical implant, the closure cap and a closure installation tool in accordance with the present invention.

FIG. 6 is an enlarged side elevational view of the implant with the cap positioned thereon and with the set screw being installed by the anti-torque tool and the set screw installation tool.

FIG. 7 illustrates the implant with the closure positioned thereon and with the set screw positioned so as to lock the rod within a yoke of the implant and with the anti-torque tool and the set screw installation tool just subsequent to being removed from the closure with a broken away head of the set screw still within the set screw installation tool.

FIG. 8 is a cross sectional view of the implant, closure and set screw, after completion of installation, taken along line 8—8 of FIG. 7.

DETAILED DESCRIPTION OF THE INVENTION

Figure 4:
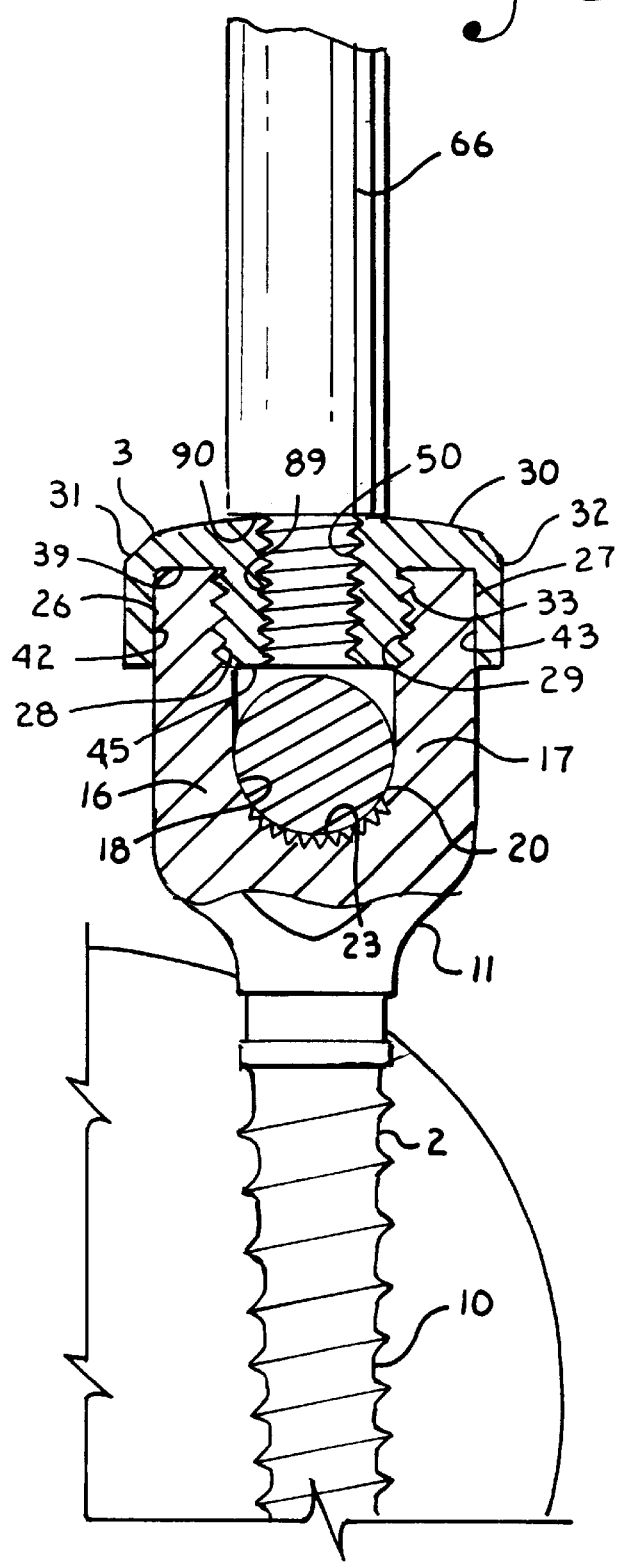
FIG. 4 is an enlarged and fragmentary side elevational view of the medical implant installed in the vertebra and with the closure cap in the process of being placed on the implant with the installation tool attached to the closure cap and with portions broken away to show detail thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a closure in accordance with the present invention utilized in conjunction with an "open" type bone screw 2. The closure 1 generally includes a closure cap 3 and a set screw 4. The various elements including the bone screw 2, closure cap 3 and set screw 4 are shown before installation in an exploded view in FIG. 1.

The present invention is illustrated in conjunction with the bone screw 2, although it is foreseen that the closure 1 could be used in conjunction with other types of medical implants that have an open end for receiving a rod or the like to allow connection between various implants of an overall implant system.

Figure 2:
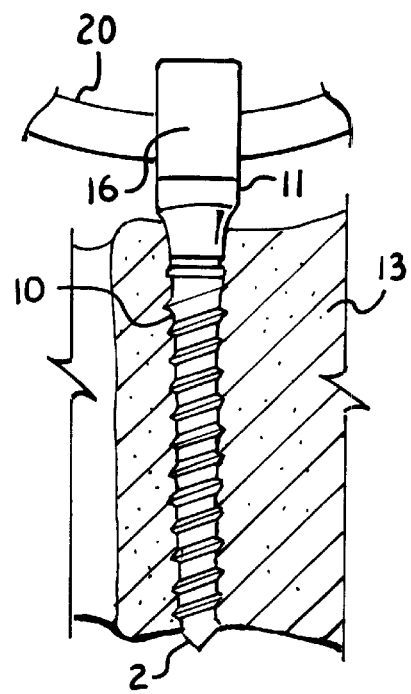
FIG. 2 is a fragmentary front elevational view of the medical implant shown positioned within a vertebra with portions broken away to show placement of the implant and having a rod positioned within an open end of the implant prior to installation of the closure.

In the illustrated embodiment, the bone screw 2 has a shank 10 and a head 11. The shank 10 is threaded and is received in a vertebral body 13 that is part of a vertebra in a patient's spinal column. The threaded shank 10 is inserted in the vertebral body 13, as is shown in FIGS. 2 and 4 with the head 11 extending from the vertebral body 13. The head 13 has a pair of upright branches or arms 16 and 17 that are generally equally spaced and form a channel 18 therebetween. In general the head 13 is shaped like a yoke for receiving a cylindrical and elongate rod 20 or other connectors associated with the medical implant system. The bottom of the channel 18 forms a seat 23 for receiving the rod 20 and may be grooved, knurled or otherwise surfaced so as to increase friction between the rod 20 and the seat 23.

The rod 20 is laid into the seat 23 by passage through an open mouth 24 of the channel 18. Each of the arms 16 and 17 have radially outward surfaces 26 and 27 and threaded radially inward surfaces 28 and 29. The threaded surfaces 28 and 29 generally face each other and are not identically threaded. In particular, the threads on the surfaces 28 and 29 are designed to allow mating with a mateable threaded circular structure, and although the pitch of the threads on the threaded surfaces 28 and 29 are similar, the positioning of the threads will be slightly different on each side to adjust for mating with a normally threaded structure to allow the structure to rotate and threadedly advance along the threads of the surfaces 28 and 29.

The rod 20 is normally not linear, but rather is curved to follow the curvature of the patient's spine, as is seen in FIG. 2. FIG. 2 is a side view illustrating the rod as it is initially placed in the bone screw channel 18 and before placement of the closure 1 thereover to capture the rod 20 in the channel 18.

The closure cap 3 includes a generally rectangular shaped body or plate 30, a pair of side flanges 31 and 32 depending from opposite ends of the plate 30 and a central cylindrical shaped member or boss 33 also depending from the plate 30.

The plate 30 is relatively thin from top to bottom and is illustrated as being substantially rectangular in shape (in horizontal cross-section) with a slight radius at the top to improve the strength thereof with opposite ends radiused. Although the plate 30 is illustrated as being generally rectangular in horizontal cross-section, such a shape is not required in accordance with the invention. The main criteria for the plate 30 is that it be longer from side to side where the side flanges 31 and 32 are attached than in width. This allows the closure cap 3 to have a comparatively thin profile relative to elements of the implant system that are located adjacent to the closure cap 3 when the entire system is fully installed. For example, the outermost edges of the side flanges 31 and 32 may in some instances be spaced twice as wide as the width of the closure cap 3 that is perpendicular thereto. The plate 30 has an upper surface 37 that is arcuate and a lower surface 38 that is flat. Near whereat the side flanges 31 and 32 attach to the plate 30 is a region 39 on the lower surface that may, but is not required to, abut or engage the upper ends of the arms 16 and 17, when assembly is complete. The region 39 is on either side of the cylinder 33 spaced between the cylinder 33 and the side flanges 31 and 32.

The side flanges 31 and 32 each have radially inward facing surfaces of 42 and 43 that each form a partial cylindrical surface in such a way as to mate with inner surfaces of the arms 28 and 29. Consequently, the portion of the closure cap 3 that includes the plate 30 and side flanges 31 and 32 is very much like a full cylindrical or circular shaped closure cap that is placed about the outside of the arms 16 and 17, except that outer opposed segments have been removed to make the closure cap 3 thinner in profile.

The boss 33 is mounted in the center of the plate 30 and extends toward the seat 23 when the closure cap 3 is fully mounted on the bone screw 2. The boss 33 has a cylindrical shaped outer surface 45 that is threaded and is carefully sized so as to allow the boss 33 to be screwed between the arms 16 and 17 during installation of the closure cap 3 on the bone screw 2. In this manner the boss 33 prevents the arms 16 and 17 from bending inwardly toward one another during use of the bone screw 2, while the flanges 31 and 32 prevent the arms 16 and 17 from bending outwardly relative to each other during usage. The boss 33 also has a lower surface 45 and an upper surface that is fixedly secured to the underside of the plate 30 and the boss lower surface 45 becomes closely spaced from or in touching engagement with the rod 20 during use. Because the set screw 4 is used to lock the position of the rod 20 relative to the bone screw 2, the closure cap 3 does not have to be against the rod 20, but only capture rod 20 in the head 11.

A threaded bore 50 passes through the plate 30 and the boss 33 from top to bottom thereof and centrally with respect to the closure cap 3.

The set screw 4 has a base 53 and a head 54. The set screw base 53 has an outer cylindrical surface 56 that is threaded to be threadably received within the closure cap bore 50 during use. The base 53 also includes a lower tip or point 57. The set screw head 54 includes a polyhedral shaped radially outward surface which in the illustrated embodiment is a hexagonal shaped surface 60 to allow a tool to have purchase or to grip of the set screw 4 during insertion. The head 54 is joined to the base 53 by a breakaway region 61.

Installation of the set screw 4 into the closure cap 3 is illustrated in FIG. 6. Illustrated in FIG. 7 is the set screw base 53 fully inserted into the cap 3 with the head 54 broken away. That is, as the set screw 4 is inserted into the closure cap 3 it is advanced in the bore 50 until the tip 57 engages the rod 20, thereafter the set screw 4 is further rotated or torqued until sufficient torque is applied such that the head 54 breaks away from the base 53 at a preselected torque which may be on the order of 100 inch pounds.

The set screw 4 has a diameter that is substantially smaller than the space between the arms 16 and 17. In this manner the set screw 4 sits and biases against a relatively short length of the rod 23 in comparison to the boss 33. Therefore, even if the rod 23 is significantly bent, the set screw 4 engages such a small length of the rod 20 that it is less susceptible to loosening of either the rod 20 relative to the bone screw 2 or of the rod 20 relative to the set screw 4 when the rod 20 flexes during use. Preferably, the point 57 of the set screw 4 bites into the rod 20 directly opposite whereat the rod 20 abuttingly engages the seat 23.

A set of tools is provided for both installing and removing the closure 1 from the bone screw 2. The tools include a closure cap installing or holding tool 66, a set screw torquing tool 68, a closure cap anti-torque tool 69 and a removal tool 71.

The closure cap installing or holding tool 66 includes an elongate shaft 88 ending in a threaded cylindrical mount 89 at a shoulder 90. The threads on the mount 89 are sized and the tool 66 is also sized and shaped so that the mount 89 can be operably threaded into the closure cap bore 50.

A gripable head 91 for operably rotating the tool 68 is positioned on the shaft 88 opposite the mount 89. The mount 89 can be threaded into the closure cap bore 50 and snugged down thereagainst so as to temporarily secure the closure cap 3 to the closure cap holding tool 66. The closure cap 3 is then threaded on the bone screw 2, with the rod 20 received in the seat 23 of the bone screw 2, by rotating the holding tool 66. Once the closure cap 3 has been tightened onto the bone screw 2, for example, to the position where the plate lower surface 38 engages the upper end of the bone screw arms 16 and 17, the holding tool 66 is removed by rotating the tool 66 counterclockwise to release it from the closure cap 3, leaving the closure 3 mounted on the bone screw 2 and configured so that the widest part of the closure 3 is generally perpendicular to the axis of the rod 20 at the seat 23.

The second stage in the process of installing the closure cap 3 requires installation of the set screw 4. This is accomplished by the combined usage of the set screw torquing tool 68 and the anti-torquing tool 69.

Figure 5:
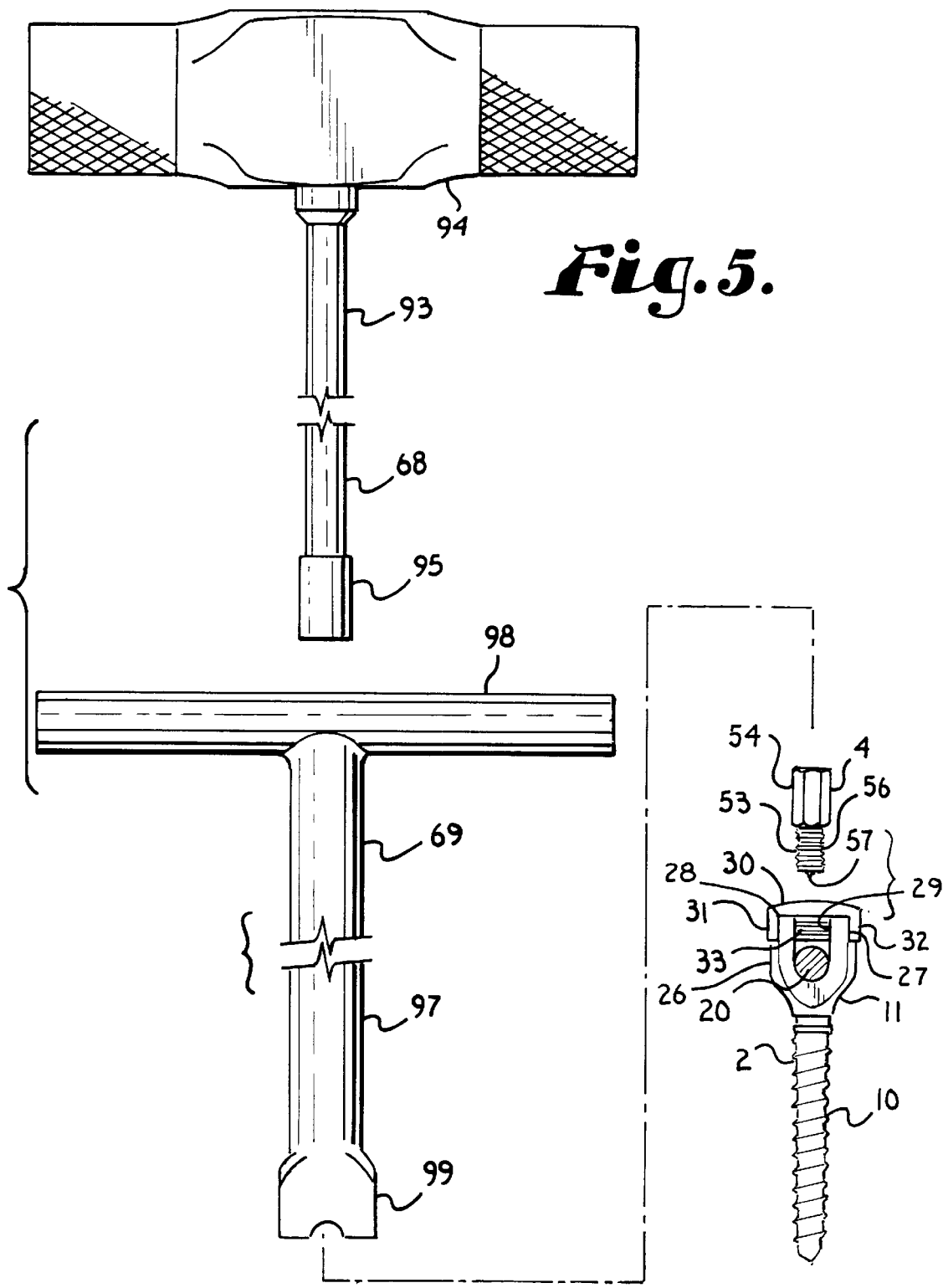
FIG. 5 is an exploded side elevational view of the bone screw with the cap positioned thereon and showing the set screw with an anti-torque tool and a set screw installation tool that are both used cooperatively to install the set screw.
Figure 9:
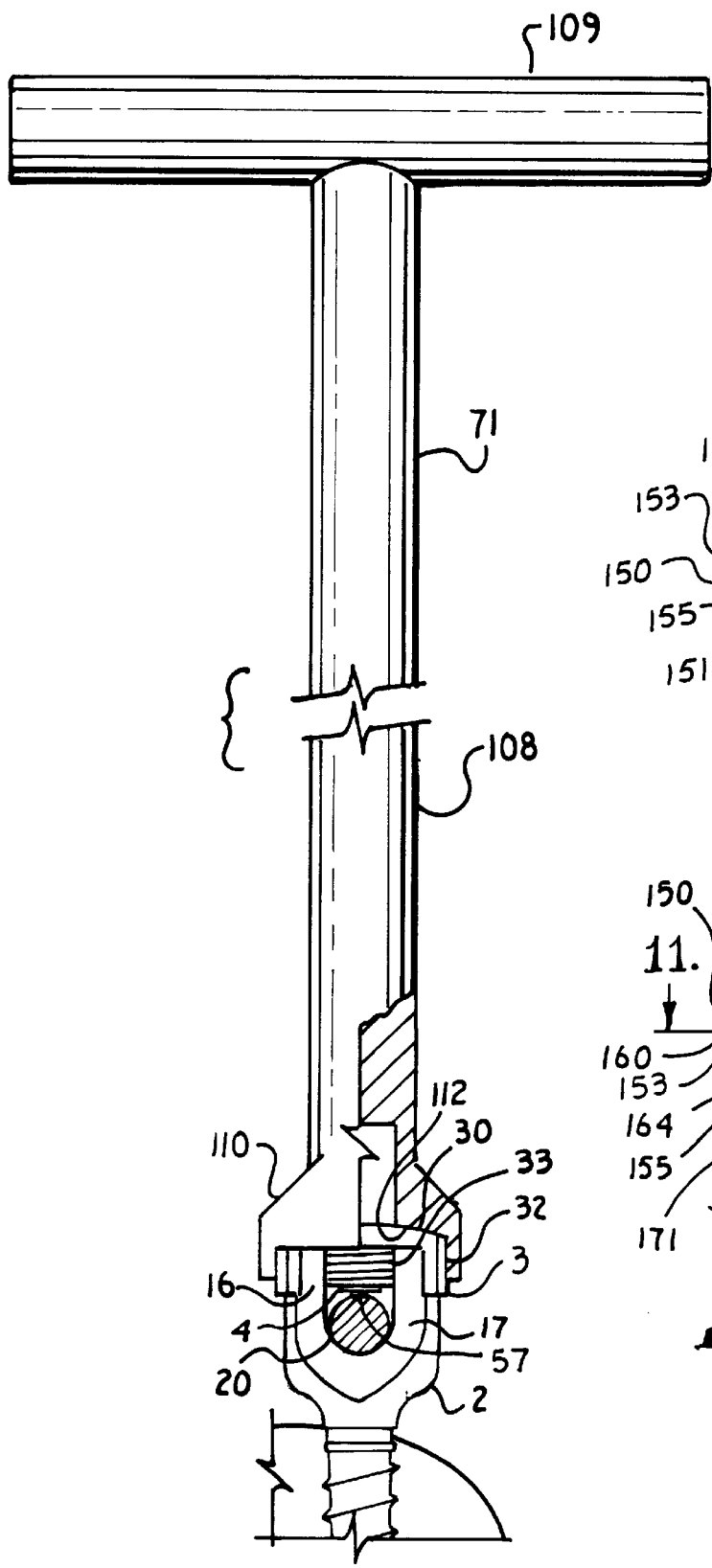
FIG. 9 is a side elevational view of the implant with the closure thereon and showing a closure cap removing tool positioned on the closure cap.

The set screw torquing tool 68 is seen in FIG. 5 and includes an elongate shaft 93 ending at one end with a fixed torquing handle 94 and at the opposite end with a socket 95 that is sized and shaped to snugly receive the set screw head 54. That is, the socket 95 will normally have the same polyhedral cross-section as the head 54 to allow it to firmly grip the head 54 and allow the torquing tool 68 to rotate the head.

The anti-torquing tool 69 also includes a shaft 97 attached at one end to a handle 98 for gripping and having a head 99 at an opposite end. A bore 100 extends through the shaft 97 to receive the tool 68. The anti-torquing tool head 99 is sized and shaped to fit over both the closure cap 3 and about the tops of the bone screw arms 16 and 17, so as to hold the cap 3 in place relative to the screw 2 and to operably prevent rotation of the closure cap 3 relative to the arms 16 and 17, when the anti-torquing tool 69 is installed thereover. A central arch 103 allows the head 99 to be positioned over the rod 20, as is shown in FIG. 6.

Also as is shown in FIG. 6, the set screw torquing tool 68 is positioned through the bore 100 of the anti-torquing tool 69 with the anti-torquing tool 69 positioned over the combined closure cap 3 and on top of the bone screw 2. The torquing tool 68 is specifically positioned on and operatively engages the set screw head 54 and is rotated clockwise, so as to drive the set screw 4 into the bore 50. The anti-torquing tool 69 is simultaneously held by the installer so that the closure cap 3 does not rotate relative to the bone screw 2 during installation of the set screw 4. The set screw 4 eventually engages the rod 20 and torque is continuously applied and increased to the set screw 4 until a predetermined torque is achieved at which time the set screw head 54 breaks from the base 52, such as is illustrated in FIG. 7. The set screw base 53 is then positively set against the rod 20 and secures and locks the rod 20 in place. The set screw tip or point 57 is preferably positioned opposite a location 104 where the rod 20 touches the seat 23. In this manner, the set screw base 53 securely and tightly holds the rod 20 relative to the bone screw 2 even when ends of the rod 20 flex.

It is sometimes necessary for a closure device 1 to be removed from a bone screw 2 for various reasons. The removal tool 71 is provided for this purpose.

The removal tool 71 includes an elongate shaft 108 terminating at one end in a handle that can be rotated by a user and at an opposite end in a head 110. The head 110 includes an internal cavity 112 that is substantially sized and shaped to snugly receive the closure cap 3. The removal tool 71 is placed such that the closure cap 3 is received in the cavity 112 And rotated counterclockwise until free of the bone screw 2.

Figure 11:
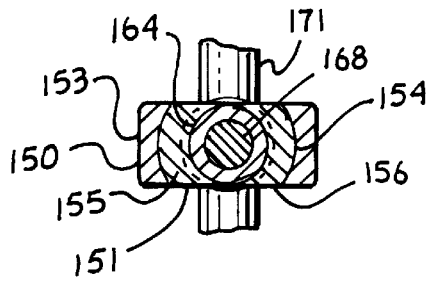
FIG. 11 is a cross sectional view of the implant, modified closure cap and set screw, taken along line 11-11 of FIG. 10.
Figure 10:
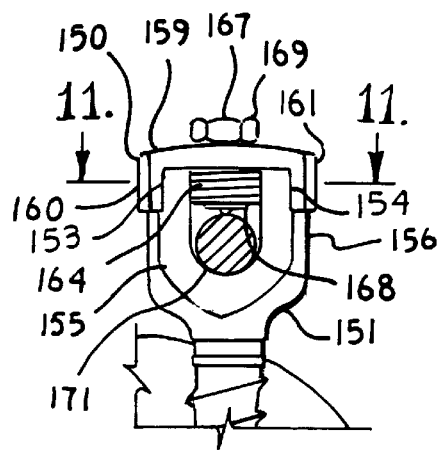
FIG. 10 is a side elevational view of an implant in accordance with the invention with a modified closure cap and a modified set screw.

Shown in FIGS. 10 and 11 is a second embodiment of a closure according to the present invention which is generally identified by the reference numeral 150. The second closure 150 is in many ways similar to the closure 1 of the previous embodiment and is installed and generally removed by the same tools, as described for the previous embodiment. Further, many of the parts of the closure 150 are the same as the parts for closure 1 and, therefore, great detail will not be utilized to describe the similar parts. Further, the closure 150 is installed on a bone screw 151 that is very similar to the bone screw 2 and only dissimilar parts will be described in detail herein.

In particular, the bone screw 151 is essentially the same as bone screw 2. The closure cap 150 has a plate 159 and side flanges 160 and 161. The closure 150 includes a cylinder or boss 164 that depends from the plate 159 in a similar fashion, as described with respect to the previous embodiment.

The second closure 150 differs from the first embodiment primarily in that it includes a set screw 167 that is a non-break-off type of set screw. That is, the set screw 167 includes a threaded body 168 and head 169 that remains attached to the body 168 once the set screw has been fully installed and torqued to a desired torque against a rod 171.

It is foreseen that the flange facing surfaces 42 and 43 and the bone screw arm outer surfaces 26 and 27 could also be matingly threaded so that not only the boss 33 screws into the threads of the interior surfaces 28 and 29 but the flanges 31 and 32 would also threadedly screw onto the exterior of the arms 16 and 17.

It is to be understood that while certain forms of the present invention have been illustrated and described herein, it is not to be limited to the specific forms or arrangement of parts described and shown.

What is claimed and desired to be secured by Letters Patent is as follows:

1. A closure cap for operably closing an open ended medical implant by being threadably received on a pair of spaced arms of such an implant in combination with said medical implant; said implant having an open head with a pair of spaced and interiorly threaded upright arms; the cap comprising:

a) a top plate having a central axis and a side to side width and a length; said plate being substantially greater in length during use in the direction of said arms compared to said width;

b) a radially outward threaded cylindrical shaped boss depending from said plate and adapted to be threadably received on said arms; and c) a pair of flanges depending from said plate and being spaced from and on opposite sides of said boss; said flanges being sized and shaped to abut against the outside of the implant arms during use to maintain spacing of the arms when said boss is screwed between said arms; said flanges further being sized and shaped to not extend substantially in width beyond said arms so as to maintain and overall side to side low profile for the cap.

2. The closure according to claim 1 wherein:

a) said plate and said flanges are sized and shaped in width to be generally equal to or less than the width of the implant arms when installed thereon.

3. The closure according to claim 1 wherein:

a) said plate is substantially longer in comparison to a side to side width of said plate.

4. The closure according to claim 3 wherein:

a) said plate is at least twice as long as wide.

5. The closure according to claim 1 wherein:

a) said flanges are spaced and discontinuous relative to each other.

6. The closure according to claim 5 wherein:

a) said plate is circular in horizontal cross-section except with opposed and generally equally sized sectors missing.

7. The closure according to claim 1 wherein:

a) said flanges depend from opposite ends of said plate and are sized and shaped to cover said arms respectively without extending outwardly on either side of a respective arm during use.

8. The closure according to claim 1 wherein:

a) said arms are interiorly radiused to conform to and threadedly receive the threaded cylindrical boss.

9. The cap and implant combination according to claim 1 wherein:

a) said flanges are spaced from one another and positioned to each engage only one arm of the implant when fully assembled.

10. A closure cap for operably closing an open ended medical implant by being threadably received on a pair of spaced arms of such an implant; the cap comprising:

a) a top plate having a central axis and a side to side width and a length; said plate being substantially greater in length during use in the direction of said arms compared to said width;

b) a radially outward threaded cylindrical shaped boss depending from said plate and adapted to be threadably received on said arms; and c) a pair of flanges depending from said plate and being spaced from and on opposite sides of said boss; said flanges being sized and shaped to so as to extend along and be snugly received over radially outer surfaces of respective arms and so as to abut against the outside of the implant arms during use to maintain spacing of the arms when said boss is screwed between said arms; said flanges further being sized and shaped to not extend substantially in width beyond said arms so as to maintain and overall side to side low profile for the cap.

11. A medical device comprising:

a) a medical implant having an open head with a pair of spaced arms, each having a radially inward surface and an outward surface; the interior surface of each said arms being arced and threaded;

b) a closure cap having an upper plate, a central cylindrical boss depending from said plate and a pair of flanges depending from opposite ends of said plate; said plate having a central axis and a side to side width and a length; said plate being substantially greater in length during use in the direction of said arms compared to said width c) said boss having a radially outward threaded surface that is sized and shaped to be threadedly received between the interior surfaces of said arms; and d) said flanges being sized and shaped to be snugly received over the outer surfaces of said arms during use; said flanges further being sized and shaped to not extend substantially in width beyond. said arms so as to maintain and overall side to side low profile for the cap.

12. The device according to claim 11 wherein:

a) said flanges are sized and shaped to be positioned over the external surfaces of said arms during use without extending outwardly to either side of a respective arm.

13. A closure cap for operably closing an open ended medical implant by being threadably received on a pair of spaced arms of such an implant; the cap comprising:

a) a top plate;

b) a radially outward threaded cylindrical shaped boss depending from said plate and adapted to be threadably received on said arms; said plate and boss include a central threaded bore;

c) a pair of flanges depending from said plate and being spaced from and on opposite sides of said boss; said flanges being sized and shaped to abut against the outside of the implant arms during use to maintain spacing of the arms when said boss is screwed between said arms; and d. a threaded set screw matingly received in said bore.

* * * * *